(12) United States Patent
Code

(10) Patent No.: US 7,867,510 B2
(45) Date of Patent: Jan. 11, 2011

(54) MATERIAL HAVING ANTIMICROBIAL ACTIVITY WHEN WET

(75) Inventor: Kenneth R. Code, Edmonton (CA)

(73) Assignee: BioLargo Life Technologies, Inc, Irvine, CA (US)

(*) Notice: Subject to any disclaimer, the term of this patent is extended or adjusted under 35 U.S.C. 154(b) by 1160 days.

(21) Appl. No.: 11/516,960

(22) Filed: Sep. 7, 2006

(65) Prior Publication Data

US 2008/0063694 A1    Mar. 13, 2008

(51) Int. Cl.
 *A61K 9/70* (2006.01)
(52) U.S. Cl. .................. 424/443; 424/404; 424/406; 424/409; 424/411; 424/446; 424/447; 424/637; 424/667; 424/670; 523/122
(58) Field of Classification Search .......... 424/667–671
See application file for complete search history.

(56) References Cited

U.S. PATENT DOCUMENTS

| | | | |
|---|---|---|---|
| 206,024 A | 7/1878 | Kendall | 222/432 |
| 2,134,791 A | 11/1938 | Loweke | 188/79.53 |
| 2,817,621 A * | 12/1957 | Marks et al. | 424/421 |
| 3,464,413 A | 9/1969 | Goldfarb et al. | 604/306 |
| 3,489,148 A | 1/1970 | Duncan et al. | 604/382 |
| 3,585,998 A | 6/1971 | Hayford et al. | 165/8 |
| 3,800,792 A | 4/1974 | McKnight et al. | 602/50 |
| 3,896,807 A | 7/1975 | Buchalter | 604/289 |
| 4,375,535 A | 3/1983 | Kightlinger et al. | 527/313 |
| 4,381,784 A | 5/1983 | Aberson et al. | 604/368 |
| 4,405,323 A | 9/1983 | Auerbach | 604/285 |
| 4,418,686 A | 12/1983 | Child | 604/285 |
| 4,497,930 A | 2/1985 | Yamasaki et al. | 524/556 |
| 4,675,014 A | 6/1987 | Sustmann et al. | 604/375 |
| 4,722,937 A | 2/1988 | Jacob et al. | 514/474 |
| 4,731,391 A | 3/1988 | Garvey | 521/137 |
| 5,201,326 A | 4/1993 | Kubicki et al. | 128/832 |
| 5,227,161 A | 7/1993 | Kessler | 424/94.4 |

(Continued)

FOREIGN PATENT DOCUMENTS

CA    2278959    *    1/2001

(Continued)

OTHER PUBLICATIONS

P. Kapur and M. Verma, "Determination of Iodate Ion in Presence of Cupric Ion", Industrial and Engineering Chemistry Analytical Ed.; vol. 13, No. 5 (May 1941). p. 338.

(Continued)

*Primary Examiner*—Neil Levy
(74) *Attorney, Agent, or Firm*—Mark A. Litman & Associates, P.A.

(57) ABSTRACT

An article is applied to the body of an animal (including humans) to provide both absorbency and antimicrobial activity. The article may comprise a water absorbent material; and a composition that reacts with water to produce molecular iodine. The composition provides a local concentration (in the water) of at least 10 parts per million iodine in water carried by the material (that is actual water supported by the water absorbent material) when the material has 5% by weight of water present in the water absorbent. The article may be a diaper, sanitary pad, bandage, bandaid or wrap for an animal.

6 Claims, 1 Drawing Sheet

U.S. PATENT DOCUMENTS

| | | | |
|---|---|---|---|
| 5,419,902 A | 5/1995 | Kessler | 424/94.4 |
| 5,612,045 A | 3/1997 | Syverson | 424/402 |
| 5,629,024 A | 5/1997 | Kessler et al. | 424/667 |
| 5,639,481 A | 6/1997 | Kessler et al. | 424/667 |
| 5,643,588 A | 7/1997 | Roe et al. | 424/402 |
| 5,648,075 A | 7/1997 | Kessler et al. | 424/94.4 |
| 5,772,971 A | 6/1998 | Murphy et al. | 422/292 |
| 5,849,291 A | 12/1998 | Kessler | 424/94.4 |
| 5,885,592 A | 3/1999 | Duan et al. | 424/400 |
| 5,962,029 A | 10/1999 | Duan et al. | 424/613 |
| 6,248,335 B1 | 6/2001 | Duan et al. | 424/400 |
| 6,261,577 B1 | 7/2001 | Kessler | 424/401 |
| 6,365,220 B1 | 4/2002 | Burrell et al. | 427/2.1 |
| 6,403,113 B1 | 6/2002 | Corzani | 424/404 |
| 6,403,674 B1 | 6/2002 | Schubert | 522/167 |
| 6,432,426 B2 | 8/2002 | Kessler | 424/401 |
| 6,703,536 B2 | 3/2004 | Roe et al. | 604/360 |
| 7,033,509 B2 | 4/2006 | Klein et al. | 210/753 |
| 2003/0135172 A1 | 7/2003 | Whitmore et al. | |
| 2005/0196593 A1 | 9/2005 | Campbell et al. | |
| 2008/0095812 A1 | 4/2008 | Code | |
| 2008/0145391 A1* | 6/2008 | Nelson et al. | 424/406 |
| 2009/0028915 A1* | 1/2009 | Code | 424/402 |

FOREIGN PATENT DOCUMENTS

| | | | |
|---|---|---|---|
| WO | WO 98/24486 | * | 6/1998 |
| WO | WO 02/058748 | * | 8/2002 |

OTHER PUBLICATIONS

PCT International Search Report and The Written Opinion of the Inernatoinal Searching Authority dated Sep. 18, 2009, from related patent application PCT/US2009/04248.

* cited by examiner

MATERIAL HAVING ANTIMICROBIAL ACTIVITY WHEN WET

BACKGROUND OF THE INVENTION

1. Field of the Invention

The present technology relates to the field of antimicrobial protection, particularly antimicrobial activity in close proximity to the bodies of patients, and more particularly in removable materials placed into contact with the bodies of patients.

2. Background of the Art

The growth of many microbes is assisted by or enabled by the presence of water with the microbes. Water and aqueous materials are present in events and activities of most mammalian life forms. Aqueous solutions and dispersion and emulsions are present in blood, exudates, tears, perspiration, menstrual emissions and waste emissions of mammals. These are natural events in life cycles, but may be accompanied by contact with or attack by microbes that can have significant physical effects on the animals (including humans) and their surrounding. At a minimum, growth of some microbes in aqueous materials around the animals can develop odors, disease-carrying media, infections and death or damage to the bodies of the animals.

There are many instances where aqueous materials are retained in contact with animal bodies and in which there is potential for unwanted and even dangerous and significant microbial growth or microbial introduction into the animal body. For example, in the application of materials wound dressing, menstrual products, patches, diapers, pads and the like, moisture from the animal body or ambient conditions or the materials themselves can introduce microbes to the environment and those microbes can proliferate in the vicinity of the materials when moisture is present. The uncontrolled growth of random microbes is seldom beneficial and has been the subject of significant efforts at control.

Many applications exist where it is necessary or at the very least an advantage for agents to be present which demonstrate anti-bacterial, anti-mycotic activity or both, resulting in the control of bacterial and/or fungal growth. For example, an apparatus or article as a whole or in part may have the property of suppressing bacterial and fungal growth. Control of bacterial and/or fungal growth may be through the prevention or inhibition of the growth of such microbes.

The most consistent forms of attempts at microbial control on patients are the direct application of compositions to the surface of patients likely to become infected, such as wounds, vaginal area, areas surrounding diapers and the like. Ointments, creams, tinctures, solutions and other materials have been applied directly to the patients affected areas as a treatment. These treatments generally direly apply or carry active antimicrobial materials to the site, either as a direct application of carried with a device to be secured locally to the patient. Among the type of efforts in this direction have been sources of silver ions surgical and other types of wound dressings. This aspect has been investigated and reported in U.S. Pat. No. 3,800,792. Metallic silver is incorporated into the dressing in one form or another and through dissolution silver ions are released into the treated area. U.K. Patent Application 2,134,791 discloses that composites containing various metals, such as silver, gold, palladium, platinum and tin are useful in surgical dressings, where the preferred metal is silver. It is postulated that the slow release of silver ions is facilitated by a galvanic interaction with the substrate of the dressing with added metallic or nonmetallic compounds.

European Patent Application 0206024 discloses use of very smooth coatings of various metal combinations on medical devices, such as catheters to provide some antimicrobial activity when the devices are in contact with body fluids.

U.S. Pat. No. 4,418,686 is directed to an implant active in releasing silver ions to treat a bacterial infection. In U.S. Pat. No. 4,418,686, the implant consists of a plurality of spaced-apart metallic bands on a plastic insert where the surfaces of the bands consist of alternate materials, such as silver and gold. The presence of the silver and gold metals in the presence of body fluids results in a galvanic action which is intended to release or liberate silver ions.

A variety of materials are used every day in treating or preventing infections in humans, animals and the like. For example, catheters, sutures surgical gloves, implants, bandages, diapers, diaper liners, dressings, small adhesive dressings, sanitary napkins and insoles are just a few. Normally, bandages are used as a barrier to airborne pathogenic organisms infecting a cut or wound. However, once infection occurs, the bandage is no longer of any benefit. If the bandage were provided with a broad spectrum antimicrobial agent, on the portion of the bandage which is in contact with the wound and surrounding skin, the bandage becomes an actively rather than a passively antimicrobial surface or microbial barrier. Catheters, implants, bandages, dressings and other materials, such as above, are used extensively every day by millions of people. As a result, any form of antimicrobial material incorporated into these types of devices must be safe for general unsupervised use, should avoid selection of resistant strains, and should be cost effective. Furthermore, the materials may have to retain their flexibility such as with bandages so as to be readily usable. Catheters, implants, bandages, diapers, diaper liners, dressings, and the like can be readily coated with thin films of active elements which, when in contact with body fluids, release substances and ions which stop the growth of or kill various types of microorganisms. As here described, there is no requirement to apply any outside electric current to maintain sustained levels of ion release to treat the infected area.

U.S. Pat. No. 6,365,220 A process for production of an actively antimicrobial surface for a substrate and for use in a biologically dynamic environment, such as for treating and preventing microbial infections, including a film consisting of at least an antimicrobial element and another electrochemically nobler element and which forms multitudinous galvanic cells with electrolyte-containing biological fluids, such as body fluids from wounds, etc., for releasing the antimicrobial element at the surface.

WO92/09289 teaches an improved method for treating diaper rash of neonates, infants, children and incontinent adults which entails applying to the site of diaper rash a composition comprising 15-40% of a copolymer or a derivative thereof, of a lower alkyl vinyl ether and maleic acid dispersed in a semisolid ointment base.

U.S. Pat. No. 4,381,784 discloses an absorbent device designed to absorb blood or blood-like fluids such as a sanitary napkin which is combined with a blood gelling agent which includes, amongst others, maleic anhydride copolymers.

U.S. Pat. No. 6,403,113 describes that certain copolymers can be used to control or prevent the growth of microbic agents such as bacteria and fungus. It has further been found that certain derivatives of these copolymers also have anti-bacterial and anti-mycotic properties. The finding that the copolymers of the invention and derivatives thereof which are preferably of high molecular weight can be used as anti-bacterial and/or anti-mycotic agents provides many advantages over anti-microbic agents of the prior art, in particular, due to the large molecular weight and polymeric character of the anti-microbic agents of the invention. Furthermore, the copolymers or derivatives per se or blends of said copolymers or derivatives can be formed into articles or incorporated into articles in the form of films, fibers, adhesives etc. The copolymers of the invention have a low toxicity due to their high molecular weight and possess intrinsic anti-bacterial and anti-mycotic activity.

U.S. Pat. No. 6,703,536 describes an absorbent article, at least a portion of which comprises a skin care composition of an enzyme inhibitor and is at least partially transferred from the article to the skin of a wearer of the article as a result of normal contact, wearer motion and/or body heat.

The art has also used lotions in combination with absorbent articles. Examples include: U.S. Pat. No. 3,585,998 to Hayford et al.; U.S. Pat. No. 3,464,413 to Goldfarb et al.; U.S. Pat. No. 3,896,807 to Buchalter; U.S. Pat. No. 3,489,148 to Duncan et al.; and U.S. Pat. No. 5,643,588 to Roe et al.

U.S. Pat. No. 5,643,588 describes diapers having top sheet containing lotion with Lotion compositions can comprise other optional components typically present in emollient, creams, and lotions of this type. These optional components include water, viscosity modifiers, perfumes, disinfectant antibacterial actives, pharmaceutical actives, film formers, deodorants, opacifiers, astringents, solvents and the like. In addition, stabilizers can be added to enhance the shelf life of the lotion composition such as cellulose derivatives, proteins and lecithin. All of these materials are well known in the art as additives for such formulations and can be employed, in appropriate amounts in the lotion compositions of the present invention.

There exists in the female body a complex process which maintains the vagina and physiologically related areas in a healthy state. In a female between the age of menarche and menopause, the normal vagina provides an ecosystem for a variety of microorganisms. Bacteria are the predominant type of microorganism present in the vagina; most women harbor about $10^9$ bacteria per gram of vaginal exudate. The bacterial flora of the vagina is comprised of both aerobic and anaerobic bacteria. The more commonly isolated bacteria are *Lactobacillus* species, corynebacteria, *Gardnerella vaginalis*, *Staphylococcus* species, *Peptococcus* species, aerobic and anaerobic *Streptococcal* species, and *Bacteroides* species. Other microorganisms that have been isolated from the vagina on occasion include yeast (*Candida albicans*), protozoa (*Trichomonas vaginalis*), mycoplasma (*Mycoplasma hominis*), chlamydia (*Chlamydia trachomatis*), and viruses (Herpes simplex). These latter organisms are generally associated with vaginitis or venereal disease, although they may be present in low numbers without causing symptoms. Physiological, social and idiosyncratic factors affect the quantity and species of bacteria present in the vagina. Physiological factors include age, days of the menstrual cycle, and pregnancy. For example, vaginal flora present in the vagina throughout the menstrual cycle can include lactobacilli, corynebacterium, ureaplasma, and mycoplasma. Social and idiosyncratic factors include method of birth control, sexual practices, systemic disease (e.g. diabetes), and medication. Bacterial proteins and metabolic products produced in the vagina can affect other microorganisms and the human host. For example, the vagina between menstrual periods is mildly acidic having a pH ranging from about 3.8 to about 4.5. This pH range is generally considered the most favorable condition for the maintenance of normal flora. At that pH, the vagina normally harbors the numerous species of microorganisms in a balanced ecology, playing a beneficial role in providing protection and resistance to infection and makes the vagina inhospitable to some species of bacteria such as *Staphylococcus aureus* (*S. aureus*). The low pH is a consequence of the growth of lactobacilli and their production of acidic products. Microorganisms in the vagina can also produce antimicrobial compounds such as hydrogen peroxide and bactericides directed at other bacterial species. One example is the lactocins, bacteriocin-like products of lactobacilli directed against other species of lactobacilli. Some microbial products may affect the human host. For example, *S. aureus* can produce and excrete into its environment a variety of exoproteins including enterotoxins, Toxic Shock Syndrome Toxin-1 (TSST-1), and enzymes such as proteases and lipase. There have been numerous attempts to reduce or eliminate pathogenic microorganisms and menstrually occurring TSS by incorporating into a tampon pledget one or more biostatic, biocidial, and/or detoxifying compounds. For example, L-ascorbic acid has been applied to a menstrual tampon to detoxify toxin found in the vagina of the human female during menstruation.

Incorporating glyceryl triacetate into a tampon pledget has been suggested. Others have incorporated monoesters and diesters of polyhydric aliphatic alcohols and a fatty acid containing from 8 to 18 carbon atoms. For example, glycerol monolaurate (GML) has been used to inhibit the production of *S. aureus* enterotoxins and TSST-1. However, as noted above, esterase is abundantly present in the vaginal epithelium and menstrual fluid. This esterase, in combination with esterase and lipase produced by bacteria can enzymatically degrade the esters into non-effective compounds. Until now, persons skilled in the art have not appreciated the affects of lipase and esterase on ester compounds.

U.S. Pat. No. 5,612,045 describes absorbent articles, such as catamenial tampons, for absorbing body fluids are disclosed which include an effective amount of a compound to substantially inhibit the production of exotoxins by Gram positive bacteria.

U.S. Pat. No. 4,405,323 to Auerbach discloses a tampon designed to eliminate the hazards of toxic shock syndrome and dysmenorrhea. The tampon has incorporated therein an antibacterial agent which is said to disperse on contact with body fluids and prevent development of the organisms which produce the toxins which cause toxic shock syndrome. Among the antibacterial materials disclosed for use are povidone-iodine compound, mercury, zinc, penicillin, erythromycin and nitrofurazone. (Povidone iodine is a topical preparation containing povidone and iodine, used for antisepsis of the skin.)

U.S. Pat. No. 5,201,326 describes a rod-shaped medical tampon for releasing an active substance, including (a) a tampon core of compressed fibers selected from the group consisting of cellulose fibers, cotton fibers, and acetate fibers; (b) a tampon cover surrounding said tampon core and being firmly bonded to one another by a glue, the tampon cover comprising a hardened collagen foam or a hardened gelatin foam impregnated with a retardant including a dissolved active substance to be released; and (c) a retrieval string connected to at least one of said tampon core and said tampon cover.

U.S. Pat. No. 4,722,937 method of prophylactics with respect to detoxification of *Staphylococcus aureus* and other toxins by ascorbic acid, salts and esters, topically applied by means of carriers which are otherwise regularly employed in the area where *Staphylococcus aureus* or other bacteria colonize, such as a pharmacological appliance including gauze pads, an absorbant mass or pad associated with menses, douches, and contraceptive compositions.

U.S. Pat. No. 4,675,014 describes method for absorbing bodily secretions while hindering the generation of odors and growth of microbes comprising applying a fibrous mass having copper cations bound through selected anions, preferably carboxymethyl, the amount of chemically bound copper being between 0.1 and 3% by weight. The fibrous mass can be in the form of a catamenial device, bandage, diaper, shoe liner, or the like.

SUMMARY OF THE INVENTION

An article for application, association with or attachment to the body of an animal (including humans) provides both absorbency and antimicrobial activity. The article may be a diaper, gauze, padding, sanitary napkin, wrap, bandage, bandaid or the like and may comprise a water absorbent material; and a composition that reacts with water to produce molecular iodine. The composition provides a local concentration of at least 10 parts per million iodine in water carried by the material when the material has 5% by weight of water present in the water absorbent with respect to the total weight of the water absorbent material.

DETAILED DESCRIPTION OF THE INVENTION

Figure 1:
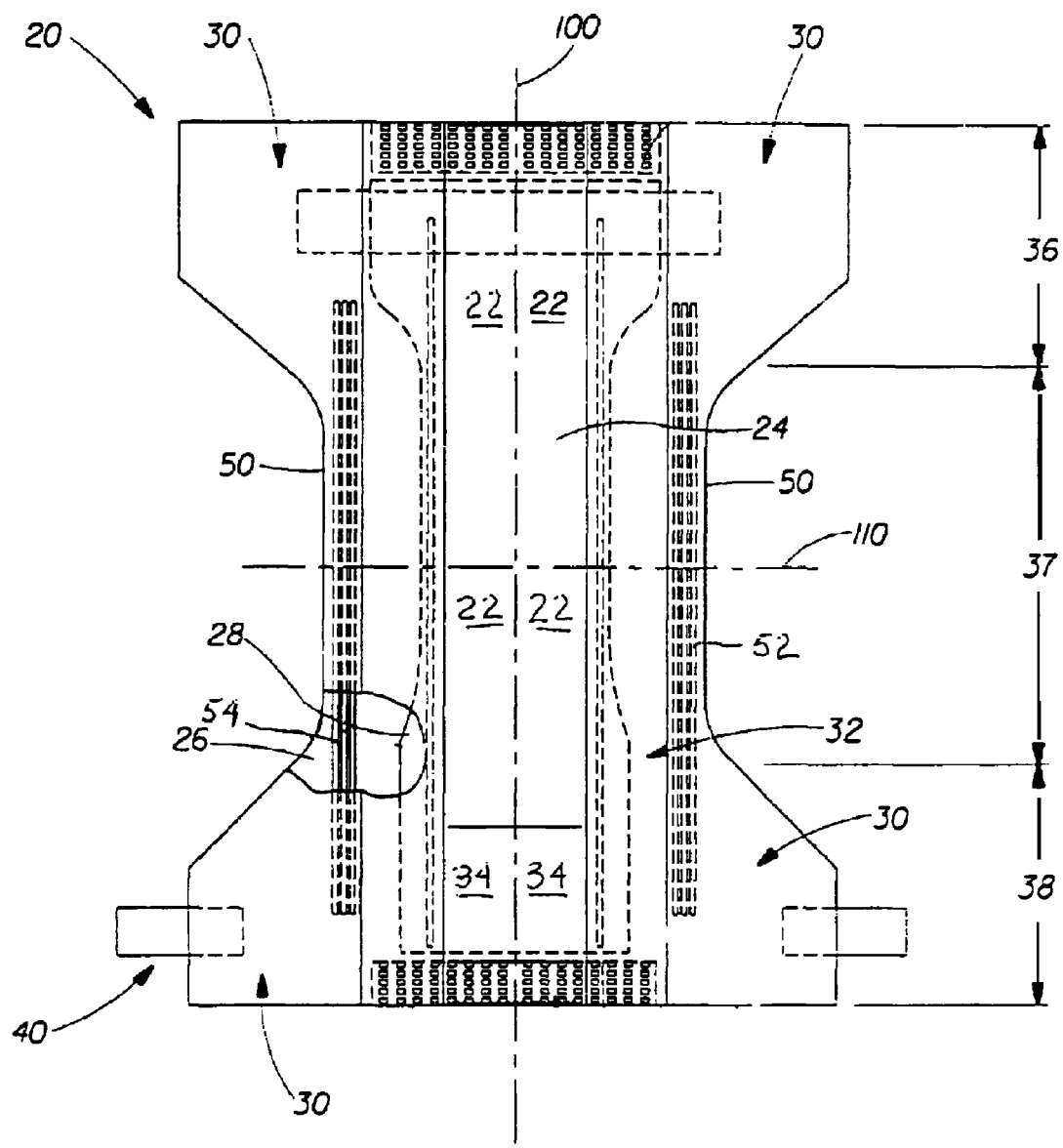
FIG. 1 shows a view of the inside of an opened diaper product and the distribution of compositions according to the present technology.

One way of providing molecular iodine ($I_2$) on site with a patient, rather than having to find a way of transporting it to a site) is to provide reactants that can readily produce molecular iodine on-site in a controllable reaction. One format of providing the molecular iodine would be through the oxidation-reduction reaction between two salts or compounds to produce the molecular iodine. It is a readily controlled environment where the reaction can be performed in an aqueous environment. One reaction that can effect this would be generically described as:

$$X^+Y^- + Z + I^- \rightarrow X^\circ + Z^+Y^- + I_2$$

In this reaction scheme, X is a metal (preferably a multivalent metal and more particularly a divalent metal), Y is an anion (preferably a multivalent anion and more preferably a divalent anion, and an anion having at least two oxygen atoms), Z is an alkali metal or alkaline cation. Examples of X are copper, iron, manganese, lead, nickel, tin, and the like, Y can be sulfate, sulfite, sulfonate, carbonate, phosphate, phosphate, nitrate, nitrie, borate, and the like, and Z can be sodium, lithium, potassium, ammonium, magnesium, aluminum, and the like. One preferred reaction would be:

$$Cu^{+2}SO_4^{-2} + K^+I^- \rightarrow Cu^\circ + K_2SO_4 + I_2$$

This reaction takes place readily in an aqueous environment and produces molecular iodine at a controlled rate. The reaction may be used by wetting, dispersing or dissolving the molecular iodide and allowing the iodine in the carrying material be released and carried to the site 9which may be the carrying material itself, such as the fabric, clay, fibers, film etc.) penetrate the area intended to be treated. The iodine may persist for sufficient time to treat the area, particularly within a wetted material on the surface of a patient. The reaction may also be used by dispersing or mixing the two ingredients into the carrying material (e.g., the fabric, fiber, film, sheet, etc.), either with additional water provided, with water of hydration on the first reactant (e.g., $X^+Y^-.nH_2O$, such as $CuSO_4.5H_2O$) or with ambient water in the carrying material. The two reactants may be physically separated from each other before being combined for application or reaction, as in separate capsules, fibers, layers or the like. The two reactants may be provided as a solid carrier medium that separates the two reactants until they are in contact with water (as in a soluble carrier such as polyvinyl alcohol, gelatin, amylase, sugars and the like, in pellet, fiber, dust, particle or block form). The two reactants may be independently coated with a soluble/dispersible coating and the two ingredients kept in a single water-penetrable layer.

Although the materials of the described technology may be provided in a vast array of materials and compositions applied to the surface of patients, such as bandages, bandaids, diapers, gauze, wraps, sanitary napkins, tampons, plugs, sheet coverings 9 e.g., on beds) and the like, the discussion will emphasize diapers and incontinence diapers for simplifying the disclosure, without intending to limit the scope of the invention.

The Technology described herein is performed by applying a solid carrier system to a patient, and awaiting the presence of sufficient water on or in the carrier system to activate the ingredients and cause the gaseous iodine to form in sufficient concentration in the solid carrier to attenuate, reduce or eliminate bacterial growth in the solid carrier. A simple format, in considering diaper-like materials for any age animal, would include at least the following formats:

1) particulate and separate reactants may be carried in the same layer of the diaper;

2) particulate and separate reactants may be carried in different layers of the diaper;

3) particulate reactants may be carried in the same pellets in an anhydrous condition in the same layer of a diaper;

4) the particulate reactants may be adhered to the same or separate fibers or films that are associated with on constitute the diaper;

5) the reactants may be carried in fiber materials dispersed throughout or partially constituting the structure of the diaper;

6) capsules or microcapsules of the reactants in water-soluble or water-dispersible shells may be distributed throughout the diaper; and 7) a film or films (water-soluble, water-dispersible or water-leachable) may carry one or more of the reactants, with the other reactant in a location that released or carried first reactant will be placed into contact with the second reactant in the presence of water.

Other formats and process may be used as long as the presence of water on the carrier system enables the generation of gaseous molecular iodine within the carrier in sufficient concentration to act as a microbicide.

The process may use the above reaction to form the molecular iodine represented by $$XY + ZI \rightarrow X^\circ + ZY + I_2$$

wherein X is a metal, Y is an anion, Z is an alkali metal or alkaline cation, or where X is a multivalent metal, Y is a multivalent anion, and Z is an alkali metal or alkaline cation, and is preferably represented by $$Cu^{+2}SO_4^{-2} + K^+I^- \rightarrow Cu^\circ + K_2SO_4 + I_2.$$

The process may be performed where the two reactants are carried in a superabsorbent polymer. The solids carriers for the two reactants may also include compositions of the present that comprise superabsorbent or non-superabsorbent polymers, natural products (e.g., papers, cellulosic solids, water-insoluble porous materials which absorb or adsorb the film-forming material within the structure, water-soluble porous materials which absorb or adsorb the film-forming material within the structure, porous containers which merely slowly release a volume of the film-forming material, porous containers which both dissolve and physically release volumes of the film-forming composition through pores, and the like. In general, selection of an effective application rate can depend on habitat depth, surface debris, emergent and surface vegetation, organic matter, microbial and algal concentration, the specific target species, and the developmental stage of the target species. Superabsorbent polymers are described, by way of non-limiting examples in U.S. Pat. Nos. 6,403,674; 4,731,391. Superabsorbent polymers, including starch graft co-polymers, are known in the art. See, for example, those described in U.S. Pat. Nos. 4,375,535 and 4,497,930 (incorporated herein by reference), which have disclosed uses as adhesives, flocculants, sizes, water-retaining materials for agriculture and water-absorbing materials for sanitary materials. However, the spectrum of advantages attendant the use of superabsorbent polymers in solid and flowable terrestrial insecticidal, pesticidal or insecticidal/pesticidal delivery compositions have gone unrecognized.

The superabsorbent polymers of the present invention are synthetic organic polymers which are solid and hydrophilic, absorbing over 100 times their weight in water. These superabsorbent polymers are typically in a powder, granule, extruded, or flake form, adapted to be blended and/or agglomerated into any shape or form.

The superabsorbent polymers may be, for example, acrylamide alkali metal acrylate co-polymers; propenenitrile homo-polymers, hydrolyzed, alkali metal salts; polymers of propenamide and propenoic acid, alkali metal salts; hydrolyzed acrylonitrile co-polymers, and starch graft co-polymers and ter-polymers thereof. All of these are designed to be hydrophilic, absorbing over 100 times their weight in water. The resulting hydrophilic polymers can absorb from over one hundred to greater than about 5000, more typically around 500 to about 1,000, times their own weight in water (measured using distilled water, pH 7.5, 25, 760 mm Hg. absorption within about 30 seconds). However, the absorption or swelling capacity and absorption or swelling time typically varies with each specific superabsorbent polymer.

One class of superabsorbent polymers include combinations of a starch and organic monomers, oligomers, polymers, co-polymers or ter-polymers. They may be manufactured in a variety of ways, for example, the methods described in U.S. Pat. Nos. 4,375,535 and 4,497,930, and can be, for example, the product of grafting corn starch (amylopectin) with acrylonitrile (an acrylic monomer or oligomer). A second class of superabsorbent polymers includes combinations of acrylamide and acrylate polymers, co-polymers and ter-polymers.

The following examples are provided as prophetic descriptions of formats for delivery of technology according to the descriptions of the present invention.

EXAMPLE 1

Fibers would extruded in a non-aqueous solvent of polyvinyl alcohol in two separate batches in combination with particulate reactants. One set of fibers would comprise 40% by weight of Copper Sulfate and the other set of fibers would comprise 40% by weight of Potassium Iodide. The two separate fibers would blended as 5% by total weight of fabric material into the fiber filled used in a diaper. The relatively low concentration (5%) of total added fiber would be expected to minimally change the properties expected from the fiber fill, except for the additional antimicrobial function, Upon accidental release of urine (an aqueous solution) into the diaper, the polyvinyl alcohol would dissolve, the two reactants would dissolve in a single solution, the reactants would react, and the gaseous iodine would be produced.

The technology described herein may be generally described as an article for application to the body of an animal (including humans) to provide both absorbency and antimicrobial activity. The article may comprise a water absorbent material; and a composition that reacts with water to produce molecular iodine. The composition provides a local concentration (in the water) of at least 10 parts per million iodine in water carried by the material (that is actual water supported by the water absorbent material) when the material has 5% by weight of water present in the water absorbent. The 5% is with respect to the total weight of water to the water absorbent material. The article may be a diaper, sanitary pad, bandage, bandaid or wrap for an animal. The water absorbing material preferably comprises water absorbing fibers. The composition that reacts with water to form molecular iodine may comprise at least two salts, one of which at least two salts comprises an iodide salt. The at least two salts may be selected from the groups consisting of a) XY and b) Z I, wherein X is a metal, Y is an anion, and Z is an alkali metal, ammonium or alkaline cation. X is preferably a divalent metal cation. Y is preferably selected from carbonate, sulfate, sulfite, phosphate, phosphate, nitrate and nitrite, and Z is preferably selected from the group consisting of lithium, potassium, calcium, magnesium, sodium and ammonium. The composition that reacts with water to form molecular iodine preferably comprises cupric sulfate and potassium iodide.

The article may have the iodine forming composition appropriately located within the article. For example, where the article is a diaper, it may have more than 70% of total composition in a central 50% of volume of the diaper. There is little need for antimicrobial activity on the portions of the diaper contacting the outer portions of the hips. Similarly, there would be little need for such activity along the waistband of the diaper. It is therefore desirable to concentrate the active materials in the diaper where the water (e.g., urine) is likely to be emitted. The iodine would migrate through the path of the water to all wetted areas.

A method of inhibiting microbial growth in an article provides a composition within the article, the composition comprising at lest two compounds that react in the presence of water to produce molecular iodine, and placing the article against the skin of an animal where an aqueous emission from the animal may occur. The method acts so that upon addition of water in an amount of between 10 and 100% by weight of the composition, a concentration of at least 10 parts per million of iodine is produced in the water in les than 15 minutes.

Another improvement would be to include starch materials into the diaper or the surface of the diaper so that the released iodine would cause the standard reaction for starch testing and a blue coloration would appear on the surface of the diaper to alert caregivers that urination had occurred.

EXAMPLE 2

Two porous films of water-soluble or water-dispersible material such as mannitol are extruded, the porosity provided by mechanical punching of the film of leaching of materials from the film, as well understood in the art. The separate films would contain 40% by weight of Copper Sulfate and 40% by weight of Potassium Iodide. The films can be used as adjacent or opposite side containers for the fiber fill (preferably with a separate non-dissolvable film).

EXAMPLE 3

Individual granules of Copper Sulfate and Potassium Iodide are coated with water-soluble/dispersible coatings, preferably in the 2-8 micron thickness range. The uncoated particles would preferably have a diameter of between 5-50 microns so that they could be carried in fiber fill for a diaper without too ready settling out of the fiber fill. The coated particles are mixed into the fiber fill, either alone or with a tacky material (on the fiber or on the particles, such as a partially dried coating on the particles) to avoid separation. The fiber particle blend would constitute the fiber fill in a diaper.

FIG. 1 shows a view of the inside of an opened diaper product 20 and the distribution of compositions according to the present technology. The diaper product 20 is shown with a longitudinal center-line 100 and a horizontal center-line 110 about which are approximately symmetrically disposed wide panels 30, adhesive tabs 40, a central absorbent sheet 24, a stretchable/flexible outer cover layer 32 that may be continuous with the wide panels 30. A sectioned area 26 exposes longitudinal elastic filaments 54 that form the elasticity of the diaper along with the crinkling pattern 52. There are significant indentations 50 on the sides of the diaper t20 to allow fitting to legs. The central absorbent sheet 24 is shown with four separate areas 22 within which there could be the heaviest concentrations of the iodine forming material, and two panels 34 that are towards a more rearward placement on a user where lower concentrations of iodine forming material could be located. Areas outside the central absorbing sheet 24 may have little or no iodine forming materials therein. As noted above, the concentration of the iodine forming materials should be centralized where liquids are more likely to be emitted into the absorbent area and be retained in the absorbent area. The upper region of the diaper and pad 36 and the lower region of the diaper and pad 38 could therefore have less total amount and less concentration of the iodine forming materials then the central area 37. These concentration variations in the vertical direction may also be reflected or substituted with similar regional variations in the horizontal direction of the diaper 20.

The concentration of the iodine forming material may be selected in the article according the ultimate needs and designs of the manufacturer, and the level of ant-bacterial effect desired. The concentration of the iodine gas in the liquid in the absorbent material is one measure of the desired results, and a further measure of the desired results is referred to in the art as the kill percentage, a measure of the percent of a specific bacteria (e.g., *E. coli*) in a liquid sample that would be killed in 5 minutes by the level of active ingredient present. An example would be that the presence of about 8 parts per million of gaseous iodine dissolved in the aqueous material in the absorbent material would have a kill percentage over 50%. It would be desired, as noted above, to have higher concentrations of gaseous iodine in the liquid so that kill percentages are at least 60%, at least 70%, at least 80% and even at least higher than 90% for targeted bacteria and other microbes. Depending upon the specific bacteria or microbe selected for the measurement, the liquid may have to be provided with at least 10 parts per million (ppm), at least 15 ppm, at least 20 ppm, or at least 25 ppm by controlling the amount of reagents added, the rate of reaction of the reagents, and other controls aimed at keeping the iodine in solution in the liquid, such as providing thickening agents or other materials that would reduce the volatility of the iodine gas from the solution.

All references cited herein are incorporated by reference in their entirety.

What is claimed:

1. An article for application to the body of an animal to provide both absorbency and antimicrobial activity comprising:
   a water absorbent material comprising a superabsorbent polymer; and
   a reactive composition comprising at least two separate particles as a first particle of a first composition of $CuSO_4$ and a second particle of a second composition of KI, the composition of the first particle and the composition of the second particle reacting with each other in the presence of water to produce molecular iodine each of the particles of the first composition being physically separated from all particles of the second composition, each of the particles of the first composition being physically dispersed with all particles of the second composition within the water absorbent material comprising a superabsorbent polymer so that application of water equal to 100% by weight of the reactive composition to the article will cause the at least two separate particles to by carried by the water and react with each other;
   the reactive composition providing a local concentration of at least 10 parts per million iodine in water carried by the material when the material has 5% by weight of water present in the water absorbent with respect to the total weight of the water absorbent material.

2. The article of claim 1 wherein the separation of the two particles is established by at least one particle being present in the article in a water-soluble or water-dispersible shell distributed throughout the article and the article comprises a super-absorbent polymer.

3. The article of claim 1 comprising a diaper, sanitary pad, bandage, band aid or wrap for an animal.

4. The article of claim 1 comprising a diaper, and where the water absorbing material comprises water absorbing, super-absorbent polymer fibers.

5. An article for application to the body of an animal to provide both absorbency and antimicrobial activity comprising:
   a water absorbent material; and
   a reactive composition comprising at least two separate particles as a first particle of a first composition and a second particle of a second composition, as a first particle of a first composition of $CuSO_4$ and a second particle of a second composition of KI, the composition of the first particle and the composition of the second particle reacting with each other with water to produce molecular iodine, each of the particles of the first composition being physically separated from all particles of the second composition so that application of water equal to 100% by weight of the reactive composition to the article will cause the at least two separate particles to by carried by the water and react with each other;
   the reactive composition providing a local concentration of at least 10 parts per million iodine in water carried by the material when the material has 5% by weight of water present in the water absorbent with respect to the total weight of the water absorbent material, and
   wherein, the two separate particles are separated by a film of a water-soluble or water-dispersible polymer that separates the article into two different regions, with the first particle exclusively in one region and the second particle exclusively in the second region.

6. The article of claim 5 wherein the separation of the two particles is established by at least one particle being present in the article in a water-soluble or water-dispersible shell distributed throughout the article and the article comprises a super-absorbent polymer.

* * * * *